US012611430B2

(12) United States Patent
Matoba et al.

(10) Patent No.: US 12,611,430 B2
(45) Date of Patent: Apr. 28, 2026

(54) THERAPEUTIC AGENT OF PERIPHERAL BLOOD FLOW DISORDER

(71) Applicants: KYOTO PREFECTURAL PUBLIC UNIVERSITY CORPORATION, Kyoto (JP); LIFE SCIENCE INSTITUTE, INC., Chiyoda-ku (JP)

(72) Inventors: Satoaki Matoba, Kyoto (JP); Mari Dezawa, Sendai (JP)

(73) Assignee: KYOTO PREFECTURAL PUBLIC UNIVERSITY CORPORATION, Kyoto (JP)

( * ) Notice: Subject to any disclaimer, the term of this patent is extended or adjusted under 35 U.S.C. 154(b) by 832 days.

(21) Appl. No.: 17/298,367

(22) PCT Filed: Nov. 29, 2019

(86) PCT No.: PCT/JP2019/046847
§ 371 (c)(1),
(2) Date: May 28, 2021

(87) PCT Pub. No.: WO2020/111249
PCT Pub. Date: Jun. 4, 2020

(65) Prior Publication Data
US 2022/0000936 A1     Jan. 6, 2022

(30) Foreign Application Priority Data
Nov. 30, 2018     (JP) ................................. 2018-225295

(51) Int. Cl.
*A61K 35/545*     (2015.01)
*A61P 9/10*     (2006.01)

(52) U.S. Cl.
CPC .............. *A61K 35/545* (2013.01); *A61P 9/10* (2018.01)

(58) Field of Classification Search
CPC . A61K 35/545; A61P 9/00; A61P 9/08; A61P 9/10
See application file for complete search history.

(56) References Cited

U.S. PATENT DOCUMENTS

| | | | |
|---|---|---|---|
| 2011/0070647 A1 | 3/2011 | Dezawa et al. | |
| 2019/0175662 A1 | 6/2019 | Saiki et al. | |

FOREIGN PATENT DOCUMENTS

| | | | | |
|---|---|---|---|---|
| CN | 102641297 A | * | 8/2012 | ............. A61K 35/28 |
| JP | 5185443 B2 | | 4/2013 | |
| WO | WO 2011/007900 A1 | | 1/2011 | |
| WO | WO-2012024296 A1 | * | 2/2012 | ........... C12N 5/0663 |
| WO | WO 2018/021515 A1 | | 2/2018 | |

OTHER PUBLICATIONS

Kondo et al. "Long-Term Clinical Outcomes Survey of Bone Marrow-Derived Cell Therapy in Critical Limb Ischemia in Japan" Circ J. Mar. 23, 2018;82(4):1168-1178 (Year: 2018).*
Araújo et al. "Use of bone marrow stem cells to treat critical ischemic limbsAraujo et al." Jornal Vascular Brasileiro, 2006, pp. 209-214, vol. 5, Issue 3 (Year: 2006).*
Extended European Search Report issued Sep. 1, 2022 in European Patent Application No. 19891644.7, 11 pages.
Iyer, Sunil R., et al., "Therapeutic Angiogenesis for Peripheral Artery Disease", JACC: Basic to Translational Science, Oct. 2017, vol. 2, No. 5, XP055953677, pp. 503-512.
Vriese, A.S. De, et al., "Autologous transplantation of bone marrow mononuclear cells for limb ischemia in a Caucasian population with atherosclerosis obliterans", Journal of Internal Medicine, Jan. 2008, vol. 263, No. 4, XP055953893, pp. 395-403.
International Search Report issued on Feb. 10, 2020 in PCT/JP2019/046847 filed on Nov. 29, 2019, 3 pages.
Hou et al., "Erythropoietin augments the efficacy of therapeutic angiogenesis induced by allogenic bone marrow stromal cells in a rat model of limb ischemia", Mol. Biol. Rep., 2010, vol. 37, pp. 1467-1475.
Liu et al., "Hypoxia Pretreatment of Bone Marrow Mesenchymal Stem Cells Facilitates Angiogenesis by Improving the Function of Endothelial Cells in Diabetic Rats with Lower Ischemia", PLoS One, 2015, vol. 10. No. 5, pp. 1-18.
Xie et al., "Transplantation of placenta-derived mesenchymal stem cells enhances angiogenesis after ischemic limn injury in mice", J. Cell. Mol. Med., 2016, vol. 20, No. 1, pp. 29-37.
Yin et al., "Umbilical Cord-Derived Mesenchymal Stem Cells Relieve Hindlimb Ischemia through Enhancing Angiogenesis in Tree Shrews", Stem Cells International, 2016, vol. 2016, Article ID 9742034, pp. 1-9.
Kuroda et al., "Unique multipotent cells in adult human mesenchymal cell populations", PNAS, 2010, vol. 107, No. 19, pp. 8639-8643.
Wakao et al., "Multilineage-differentiating stress-enduring (Muse) cells are a primary source of induced pluripotent stem cells in human fibroblasts", PNAS, 2011, vol. 108, No. 24, pp. 9875-9880.
Kuroda et al., "Isolation, culture and evaluation of multilineage-differentiating stress-enduring (Muse) cells", Nature Protocols, 2013, vol. 8, No. 7 , pp. 1391-1415.
Kondo et al., "Implantation of Adipose-Derived Regenerative Cells Enhances Ischemia-Induced Angiogenesis", Arterioscler Thromb Vasc Biol., 2009, pp. 61-66.
Matoba , "Therapeutic Angiogenesis for Peripheral Artery Disease", Journal of Kyoto Prefectural University of Medicine, 2016, vol. 125, No. 11, pp. 759-767, 10 total pages (with English Abstract).
Japanese Office Action issued Oct. 3, 2023 in Japanese Application 2020-557865, (with unedited computer-generated English translation), 8 pages.

(Continued)

*Primary Examiner* — Titilayo Moloye
(74) *Attorney, Agent, or Firm* — Oblon, McClelland, Maier & Neustadt, L.L.P.

(57) ABSTRACT

A cell product may be used for treating a peripheral blood flow disorder, and the cell product may include an SSEA-3-positive pluripotent stem cells (Muse cells) derived from a mesenchymal tissue in a living body or a cultured mesenchymal cell. The peripheral blood flow disorder is preferably a peripheral arterial disease, more preferably chronic arterial obstruction in a limb.

14 Claims, 4 Drawing Sheets

(56) References Cited

OTHER PUBLICATIONS

Nishihara, Shoko, "The Function of Glycan Structures Expressed on Embryonic Stem Cells", Trends in Glycoscience and Glycotechnology, vol. 21, No. 120, 2009, pp. 207-218.

Muramatsu, Takashi et al., "Carbohydrate Markers of ES Cells", Trends in Glycoscience and Glycotechnology, vol. 21, No. 120, 2009, pp. 197-206.

Singaporean Office Action issued on Nov. 4, 2022 in Singaporean Patent Application No. 11202105686U, 10 pages.

Matoba et al., "Therapeutic Angiogenesis for Peripheral Artery Diseases by Autologous Bone Marrow Cell Transplantation", Current Pharmaceutical Design, 2009, vol. 15, No. 24, pp. 2769-2777.

Combined Chinese Office Action and Search Report issued Dec. 11, 2023, in corresponding Chinese Patent Application No. 201980078419.X (with English Translation of Category of Cited Documents), 16 pages.

A. Liew et al., "Therapeutic potential for mesenchymal stem cell transplantation in critical limb ischemia", Stem Cell Research & Therapy, 2012, vol. 3, No. 4, 14 pages.

Goitsuka, "Mesenchymal stromal cells: a regulator for hematopoiesis and its potential application", The Journal of Farm Animal in Infectious Disease, vol. 5, No. 2, 2016, pp. 69-74 with English abstract (see p. 74) and partial English translation for p. 69, right column, lines 7-9.

Dezawa, "Muse Cells Provide the Pluripotency of Mesenchymal Stem Cells: Direct Contribution of Muse Cells to Tissue Regeneration", Cell Transplantation, vol. 25, pp. 849-861, 2016.

Hori et al, "Intravenous administration of human Muse cells recovers blood flow in a mouse model of hindlimb ischemia", Frontiers in Cardiovascular Medicine, Nov. 11, 2022, DOI 10.3389/fcvm.2022.981088.

* cited by examiner

THERAPEUTIC AGENT OF PERIPHERAL BLOOD FLOW DISORDER

CROSS-REFERENCE TO RELATED APPLICATIONS

The present application is the national stage of international application PCT/JP2019/046847, filed on Nov. 29, 2019, and claims the benefit of the filing date of Japanese Appl. No. 2018-225295, filed on Nov. 30, 2018.

TECHNICAL FIELD

The present invention relates to a cell product in regenerative therapy. More specifically, the present invention relates to a cell product comprising a pluripotent stem cell that is effective in therapeutic angiogenesis for peripheral blood flow disorders such as peripheral arterial diseases.

BACKGROUND ART

People aged 65 or older is increasing in the population ratio at a much faster rate than predicted.

At the same time, the society has drastically changed its disease structure due to the westernization of diet and changes towards lifestyle mainly based on an automobile society, generating a new concept of lifestyle diseases such as metabolic syndrome. In particular, there is an increase in atherosclerotic disease, thereby leading to an increase in peripheral arterial disease (PAD) as well as ischemic heart disease.

PAD mainly refers to chronic arterial obstruction in limb, including arteriosclerosis obliterans (ASO), thromboangiitis obliterans (TAO, also known as Buerger's disease), and popliteal artery entrapment syndrome.

PAD can manifest itself as a foot condition called limb ischemia. However, it is not just a foot disease, but manifests itself as limb ischemia caused by peripheral vascular occlusion due to arteriosclerosis resulted from aging or diabetes mellitus. Thus, PAD is often accompanied by an ischemic heart disease or a brain disease that is also an atherosclerotic disease. PAD shows a very poor prognosis and a mortality rate that is said to be higher than that of malignant tumors. Early detection and appropriate treatment are important for PAD.

Current therapeutic strategies for PAD include those addressing circulatory disorders in lower limb, those addressing major organs of the body (brain, heart, and kidneys), and those addressing risk factors for arteriosclerosis (e.g., smoking, diabetes mellitus, hyperlipidemia, hypertension, obesity, lack of exercise, and stress). Methods for treating PAD are largely classified into medical treatment and surgical treatment.

Medical treatment for PAD includes physical therapies such as kinesiotherapy and thermotherapy; and drug therapies including antiplatelet drugs, antithrombotic drugs, and vasodilator drugs such as cilostazol, beraprost sodium, sarpogrelate hydrochloride, ticlopidine hydrochloride, ethyl icosapentate, alprostadil, alprostadil alfadex, argatroban, batroxobin, and pentoxifylline.

Surgical treatment for PAD includes endovascular therapies such as balloon dilatation, stent implantation, and atherectomy; and surgeries such as thromboendarterectomy, bypass surgery, and sympathectomy.

However, the above-described medical treatment or surgical treatment may often be ineffective for the case of severe necrosis in lower limbs. There is no end to the number of patients who have to undergo life-saving amputation in such a case.

Accordingly, there is a demand for a novel method of treating PAD, including arteriosclerosis obliterans (ASO), thromboangiitis obliterans (TAO, also known as Buerger's disease), and popliteal artery entrapment syndrome, which allows for regeneration of blood vessels, resulting in, for example, improvement in lower limb ischemia.

In recent years, studies have also been conducted on treatment of PAD by regenerative therapy.

One of such studies has reported the presence of endothelial progenitor cells that can be differentiated into vascular endothelial cells in adult bone-marrow and peripheral blood mononuclear cells, demonstrating that transplantation of bone marrow-derived mononuclear cells increases the blood flow to lower limbs in an animal model of lower limb ischemia through angiogenesis and development of collateral circulation (Non-patent Document 1).

However, it has been demonstrated that the therapy by transplantation of bone marrow-derived mononuclear cells needs collection of a large quantity of bone marrow aspirate and thus is extensively invasive. Also, it has been demonstrated that because of the cells being freshly isolated, there is individual variation in the amounts of stem cells and progenitor cells in bone marrow cells, which leads to large difference in the clinical effects.

Further, studies on regenerative therapy using mesenchymal stem cells have reported that transplantation of mesenchymal cells in rat, mouse, and rabbit models of lower limb ischemia have effects of promoting regeneration of blood vessels and ameliorating lower limb ischemia (Non-patent Documents 2 to 4).

However, these effects are not sufficient for regenerative therapy, because of, for example, lack of long-term adherence of transplanted cells to blood vessels and lack of differentiation into vessel-constituting cells.

It has been found in researches by Dezawa, one of the present inventors, that pluripotent stem cells, which are present in mesenchymal cell fractions, can be obtained without gene introduction or induction by cytokines or the like, and express SSEA-3 (Stage-Specific Embryonic Antigen-3) as a surface antigen (Multilineage-differentiating Stress Enduring cells; Muse cell), can be responsible for the pluripotency possessed by the mesenchymal cell fractions, and applied to disease treatment aimed at tissue regeneration (e.g., Patent Document 1; Non-patent Documents 5 to 7). However, it has not been demonstrated whether Muse cells could provide expected therapeutic effects in treatment of peripheral arterial disease.

PRIOR ART DOCUMENTS

Patent Documents

Patent Document 1: Japanese Patent No. 5185443
Patent Document 2: WO2011/007900

Non-Patent Documents

Non-patent Document 1: Hou X et al. Mol Biol Rep 37:1467-1475 (2010)
Non-patent Document 2: Liu J., Hao H., Xi a L., et al. Hypoxia pretreatment of bone marrow mesenchymal stem cells facilitates angiogenesis by improving the function of endothelial cells in diabetic rats with lower ischemia. PLoS ONE. 2015; 10(5)

Non-patent Document 3: Xie N., Li Z., Adesanya T. M., et al. Transplantation of placenta-derived mesenchymal stem cells enhances angiogenesis after ischemic limb injury in mice. Journal of Cellular and Molecular Medicine. 2016; 20(1):29-37

Non-patent Document 4: Cunping Yin, Yuan Liang, Jian Zhang, Guangping Ruan, Zian Li, Rongqing Pang, and Xinghua Pan, Umbilical Cord-Derived Mesenchymal Stem Cells Relieve Hindlimb Ischemia through Enhancing Angiogenesis in Tree Shrews. Stem Cells International, Volume 2016 (2016), Article ID 9742034, 9 pages Non-patent Document 5: Kuroda Y et al. Proc Natl Acad Sci USA, 2010: 107: 8639-8643.

Non-patent Document 6: Wakao S et al. Proc Natl Acad Sci USA, 2011: 108: 9875-9880.

Non-patent Document 7: Kuroda Y et al. Nat Protc, 2013: 8: 1391-1415.

Non-patent Document 8: Kondo K et al. Arterioscler. Thromb. Vasc. Biol. 2009; 29: 61-66.

SUMMARY OF THE INVENTION

Problems to be Solved by the Invention

An object of the present invention is to provide a cell product for treating peripheral blood flow disorders including peripheral arterial disease.

Means for Solving the Problems

The present inventors have found that administration of human Muse cells to an immunodeficient mouse model of hindlimb ischemia that do not reject human cells via a blood vessel or the like, or directly to a peripheral arterial site and its surroundings in the subject results in accumulation and engraftment of the Muse cells to the injured peripheral arterial site, and reconstruction of blood vessels in the impaired peripheral arterial site, thereby ameliorating or treating vascular disorders in the peripheral arterial site. The present inventors have found thus that the Muse cells can be used in treatment of peripheral blood flow disorder including peripheral arterial disease, thereby completed the present invention.

Accordingly, the present invention provides the following items [1] to [11].

[1] A cell product for treating a peripheral blood flow disorder, comprising an SSEA-3-positive pluripotent stem cell derived from a mesenchymal tissue in a living body or a cultured mesenchymal cell.

[2] The cell product of item [1], wherein the peripheral blood flow disorder is a peripheral arterial disease.

[3] The cell product of item [2], wherein the peripheral arterial disease is chronic arterial obstruction in a limb.

[4] The cell product of item [2] or [3], wherein the peripheral arterial disease is arteriosclerosis obliterans.

[5] The cell product of item [2] or [3], wherein the peripheral arterial disease is thromboangiitis obliterans (Buerger's disease).

[6] The cell product of item [2] or [3], wherein the peripheral arterial disease is popliteal artery entrapment syndrome.

[7] The cell product of any one of items [1] to [6], wherein said pluripotent stem cell is one having all of the following characteristics:
(i) having low or no telomerase activity;
(ii) capable of differentiating into any of tridermic cells;

(iii) showing no neoplastic proliferation; and
(iv) having self-renewal capacities.

[8] The cell product of any one of items [1] to [6], wherein said pluripotent stem cell is one having all of the following characteristics:
(i) SSEA-3-positive;
(ii) CD105-positive;
(iii) having low or no telomerase activity;
(iv) capable of differentiating into any of tridermic cells;
(v) showing no neoplastic proliferation; and
(vi) having self-renewal capacities.

[8] An SSEA-3-positive pluripotent stem cell derived from a mesenchymal tissue in a living body or a cultured mesenchymal cell, for use in manufacture of a cell product for treating a peripheral blood flow disorder.

[9] A method of treating a peripheral blood flow disorder, comprising administering an effective amount of the cell product of any one of items [1] to [7] to a patient in need thereof.

[10] The method of treating a peripheral blood flow disorder of item [8], wherein the cell product is administered intravenously.

[11] The method of treating a peripheral blood flow disorder of item [8] or [9], wherein the cell product is administered multiple times.

Effect of the Invention

In the present invention, Muse cells are administered to a subject suffering from a peripheral blood flow disorder such as a peripheral arterial disease via a blood vessel or the like, or directly to a peripheral vascular site and its surroundings in the subject, resulting in accumulation and engraftment of the Muse cells to the impaired peripheral vascular site, and reconstruction of blood vessels in the impaired peripheral vascular site, thereby ameliorating or treating blood flow disorders in the peripheral vascular site.

Since Muse cells can efficiently migrate and engraft to an impaired peripheral vascular site, reconstructing blood vessels at the engraftment site, they do not require induction of differentiation into cells for therapy prior to transplantation. In addition, Muse cells are non-tumorigenic and excellent in safety. Furthermore, since Muse cells do not induce any immune rejection, treatment with allogenic preparations prepared from donors is also possible. Therefore, Muse cells having the excellent characteristics as described above can provide readily feasible means for treatment of patients with a peripheral blood flow disorder such as a peripheral arterial disease.

Since mesenchymal stem cells and autologous bone marrow cells are difficult to be administered intravenously, they are generally administered via intramuscular injection. However, there is a problem, with intramuscular injection, that sequential treatment is difficult. In contrast, Muse cells and the like can be administered intravenously and thus administered at multiple times, suggesting that multiple treatment can provide better therapeutic effects than mesenchymal stem cells and autologous bone marrow cells.

DETAILED DESCRIPTION OF THE INVENTION

Figure 1:
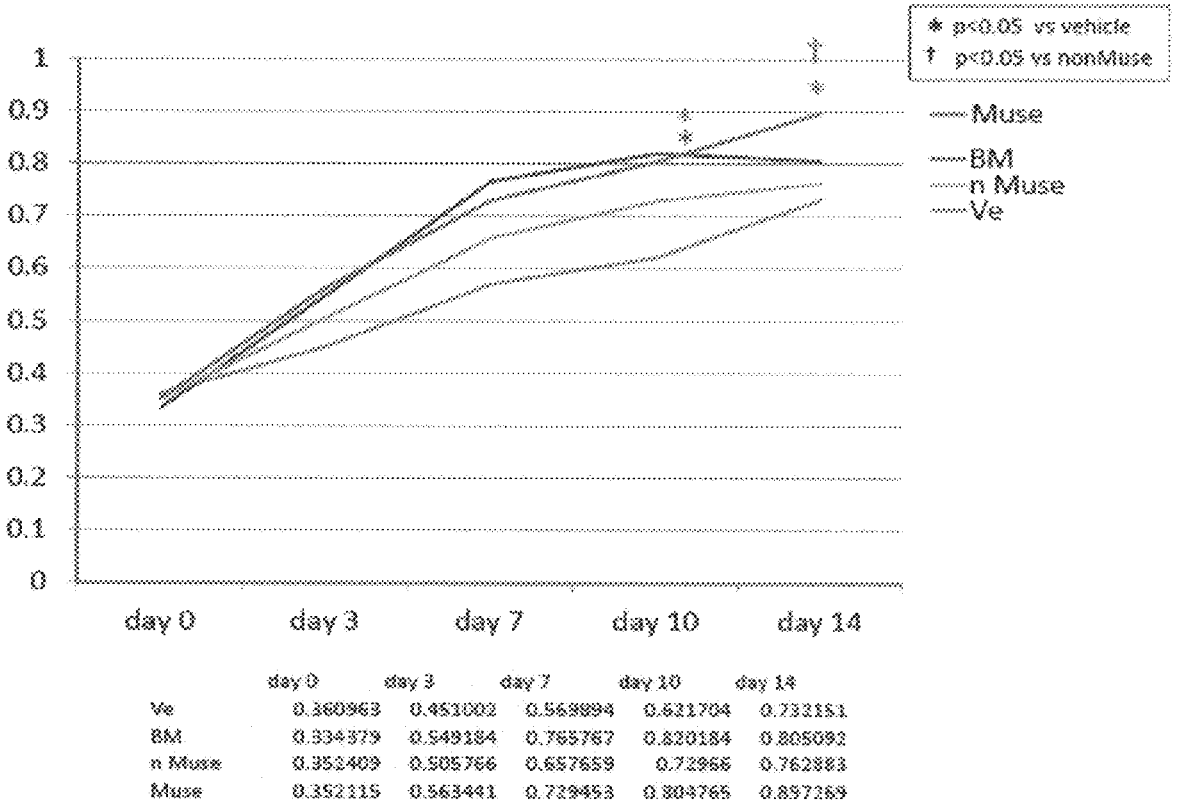
FIG. 1 is a graph showing the results of laser doppler velocimetry when the cells are administered to a mouse model of lower limb ischemia (nude mouse). The vertical axis represents ischemic/non-ischemic limb blood flow ratio. In the figure, Ve represents a vehicle, BM represents bone marrow, nMuse represents non-Muse cell, and Muse represents Muse cell.

The present invention relates to a cell product for treatment of peripheral blood flow disorders, comprising an SSEA-3-positive pluripotent stem cell (Muse cell). The present invention will be described in detail below.

1. Indications

The cell product comprising an SSEA-3-positive pluripotent stem cell (Muse cell) of the present invention is used for treatment of peripheral arterial diseases.

As used herein, the term "peripheral blood flow disorder" means a disorder caused by reduction of peripheral blood flow due to, for example, peripheral blood vessel disorders and sympathetic nerve disorders.

The peripheral blood vessel disorders include peripheral arterial diseases (PAD) and peripheral venous diseases.

The term "peripheral arterial diseases" includes organic peripheral arterial diseases and functional peripheral arterial diseases. The organic peripheral arterial diseases include arteriosclerosis obliterans (ASO), thromboangiitis obliterans (TAO, also known as Buerger's diseases), acute arterial occlusion (including acute arterial embolism, and acute arterial thrombosis), aortitis syndrome, Behcet's diseases, popliteal artery entrapment syndrome, adventitial cystic disease of the popliteal artery, and persistent sciatic artery. The functional peripheral arterial diseases include Raynaud's diseases.

The term "peripheral arterial diseases" preferably refers to diseases corresponding to arterial obstruction in a limb, preferably including, of the diseases described above, arteriosclerosis obliterans, thromboangiitis obliterans, and popliteal artery entrapment syndrome.

Raynaud's diseases include primary Raynaud's syndrome and secondary Raynaud's syndrome, and are caused by, for example, without limitation, connective tissue diseases, injuries, vibration, thoracic outlet syndrome, chronic occlusive arterial diseases, hematologic diseases, and neurological diseases.

The term "peripheral venous diseases" include venous thrombosis (such as deep venous thrombosis), chronic venous insufficiency, varicose vein, varicose eczema, and varicose ulcer.

The sympathetic nerve disorders include abnormal sympathetic reflex, including sympathetic nerve disorders that can cause peripheral blood flow disorders, such as reflex sympathetic dystrophy, causalgia, phantom limb pain, and central pain.

2. Cell Product (1) Pluripotent Stem Cell (Muse Cell)

The pluripotent stem cell used in the cell product of the present invention is a cell that was found in human living body and named "Muse (Multilineage-differentiating Stress Enduring) cell" by Dezawa, one of the present inventors. It is known that Muse cells can be obtained from, for example, bone marrow aspirates, adipose tissues (Ogura, F., et al., Stem Cells Dev., Nov. 20, 2013 (Epub) (published on Jan. 17, 2014)) and dermal connective tissues of skin, and are also broadly present in tissues and connective tissues in organs. This cell also has both characteristics of pluripotent stem cell and mesenchymal stem cell and is identified as, for example, a cell positive for "SSEA-3 (Stage-specific embryonic antigen-3)," a cell surface marker, preferably as a double-positive cell that is positive for SSEA-3 and CD-105. Therefore, Muse cells or a cell population containing Muse cells can be isolated from living tissues using, for example, expression of SSEA-3 only or a combination of SSEA-3 and CD-105 as an index. Methods for separation and identification of, and characteristics of Muse cells have been disclosed in Patent Document 2 (WO2011/007900) in detail. Taking advantage of the high resistance of Muse cells to various external stresses, Muse cells can be selectively enriched by culturing the cells under various external stress conditions, such as under protease treatment, under hypoxic conditions, under low phosphate conditions, in a low serum concentration, under undernutrition conditions, under heat shock exposure, in the presence of toxic substances, in the presence of reactive oxygen species, under mechanical stimulation, and under pressure treatment. As used herein, pluripotent stem cells prepared from mesenchymal tissues in a living body or cultured mesenchymal tissues using SSEA-3 as an index (Muse cells), or a cell population comprising Muse cells, as a cell product for treating peripheral arterial diseases, may be simply referred to as "SSEA-3-positive cells." As used herein, the term "non-Muse cell" refers to a cell contained in a mesenchymal tissue in a living body or cultured mesenchymal cells, and may refer to a cell other than "SSEA-3-positive cell."

Muse cells or a cell population comprising Muse cells can be prepared from living tissues (e.g., mesenchymal tissues) using cell surface markers, SSEA-3, or SSEA-3 and CD-105, as an index(es). As used herein, the term "living" body means mammal living body. In the present invention, living bodies exclude fertilized egg and embryos in developmental stages before blastula stage, but include embryos in developmental stages of blastula stage or later, including fetus and blastula. Examples of the mammal include, but not limited to, primates such as human and monkey; rodents such as mouse, rat, rabbit, and guinea pig; and cat, dog, sheep, pig, cattle, horse, donkey, goat, and ferret. Muse cells to be used in the cell product of the present invention are directly isolated from living tissues using the markers, and thus are clearly distinguished from embryonic stem cells (ES cells) and iPS cells. The term "mesenchymal tissue" refers to tissues such as bone, synovial membrane, fat, blood, bone marrow, skeletal muscle, dermis, ligament, tendon, dental pulp, umbilical cord, cord blood, and amnion, as well as tissues present in various organs. For example, Muse cells can be obtained from bone marrow, skin, adipose tissues, blood, dental pulp, umbilical cord, cord blood, or amnion. For example, and preferably, a mesenchymal tissue in a living body is collected, and then Muse cells are prepared from the mesenchymal tissue and used. Alternatively, using the preparation method described above, Muse cells may be prepared from cultured mesenchymal cells such as fibroblasts or bone marrow mesenchymal stem cells.

The cell population comprising Muse cells to be used in the cell product of the present invention can also be prepared by a method comprising stimulating a mesenchymal tissue in a living body or cultured mesenchymal cells with an external stress to selectively increase cells that are resistant to the external stress, and collecting the cells with an increased abundance ratio.

The external stress may be any one of or a combination of the following: protease treatment, culturing under low oxygen concentration, culturing under low phosphate conditions, culturing under low serum concentration, culturing undernutrition conditions, culturing under heat shock exposure, culturing at low temperatures, freezing treatment, culturing in the presence of toxic substances, culturing in the presence of reactive oxygen species, culturing under mechanical stimulation, culturing under shaking, culturing under pressure treatment or physical shocks.

The protease treatment is preferably carried out for 0.5 to 36 hours in total to exert an external stress. The concentration of the protease is preferably used when cells adhered to a culture vessel are peeled off, when cell aggregates are separated into single cells, or when single cells are collected from a tissue.

Preferably, the protease is a serine protease, an aspartic protease, a cysteine protease, a metalloprotease, a glutamic protease, or an N-terminal threonine protease. More preferably, the protease is trypsin, collagenase, or Dispase.

Muse cells to be used in the cell product of the present invention may be autologous or allogeneic to a recipient who will receive the cells.

As described above, Muse cells or a cell population comprising Muse cells can be prepared from living tissues, for example, by using SSEA-3 positivity or SSEA-3 and CD-105 double positivity as an index. Human adult skin is known to comprise various types of stem cells and progenitor cells. However, Muse cells are different from these cells. These stem cells and progenitor cells include skin-derived progenitor cells (SKP), neural crest stem cells (NCSC), melanoblasts (MB), pericytes (PC), endothelial progenitor cells (EP), and adipose-derived stem cells (ADSC). Muse cells can be prepared using "non-expression" of markers unique to these cells as an index. More specifically, Muse cells can be isolated using as an index non-expression of at least one, e.g., 2, 3, 4, 5, 6, 7, 8, 9, 10, or 11, of 11 markers selected from the group consisting of CD34 (a marker for EP and ADSC), CD117 (c-kit) (a marker for MB), CD146 (a marker for PC and ADSC), CD271 (NGFR) (a marker for NCSC), NG2 (a marker for PC), vWF factor (von Willebrand factor) (a marker for EP), Sox10 (a marker for NCSC), Snail (a marker for SKP), Slug (a marker for SKP), Tyrp1 (a marker for MB), and Dct (a marker for MB). Muse cells can be prepared by using as an index non-expression of, for example, without limitation, CD117 and CD146; CD117, CD146, NG2, CD34, vWF, and CD271; or the above-described 11 markers.

Muse cells having the above-described characteristics and used in the cell product of the present invention may also have at least one selected from the group consisting of the following characteristics:

(i) having low or no telomerase activity;
(ii) capable of differentiating into any of tridermic cells;
(iii) showing no neoplastic proliferation; and
(iv) having self-renewal capacities.

Preferably, Muse cells to be used in the cell product of the present invention has all of the characteristics described above.

With respect to (i) above, the phrase "having low or no telomerase activity" means that the telomerase activity is low or undetectable when detected using, for example, TRAPEZE XL telomerase detection kit (Millipore Corporation). Having "low" telomerase activity means, for example, having a telomerase activity comparable to somatic human fibroblast, or having $1/5$ or less telomerase activity, preferably $1/10$ or less telomerase activity, as compared with that of HeLa cell.

With respect to (ii) above, Muse cells are capable of being differentiated into tridermic cells (endodermal, mesodermal, and ectodermal cells) in vitro and in vivo, and can be differentiated into, for example, hepatocytes (including cells expressing markers of hepatoblast or hepatocyte), neurons, skeletal muscle cells, smooth muscle cells, osteocytes, or adipocytes by in vitro inductive culturing. Muse cells may also show the ability to be differentiated into tridermic cells when transplanted in testis in vivo. Further, Muse cells are capable of migrating and engrafting to injured organs (such as heart, skin, spinal cord, liver, and muscle) when transplanted into a living body via intravenous injection and being differentiated into cells depending on the tissues.

With respect to (iii) above, Muse cells are characterized in that they proliferate at a growth rate of about 1.3 days and proliferate from a single cell in suspension culture to form embryoid body-like cell aggregates, and then arrest their proliferation after about 14 days when the aggregates reach a certain size. When these embryoid body-like cell aggregates are transferred to adherent culture, the cells restart proliferation and cells proliferated from the cell aggregates expand at a growth rate of about 1.3 days. Further, Muse cells are characterized in that, when transplanted into testis, they do not become cancerous for at least half a year.

With respect to (iv) above, Muse cells have self-renewal (self-replication) capacities. The term "self-renewal," as used herein, means that the followings can be observed: differentiation into tridermic cells from cells contained in first embryoid body-like cell aggregates obtained by culturing single Muse cells in a suspension culture; as well as formation of next-generation second embryoid body-like cell aggregates by again culturing single cells in the first embryoid body-like cell aggregates in a suspension culture; and further differentiation into tridermic cells and formation of third embryoid body-like cell aggregates in a suspension culture from the second embryoid body-like cell aggregates. Self renewal may be repeated for one or more cycles.

(2) Preparation and Use of Cell Product

The cell product of the present invention can be obtained by, without limitation, suspending Muse cells or a cell population comprising Muse cells obtained in (1) above in a physiological saline or a suitable buffer solution (e.g., a phosphate buffered saline). In this case, when only small numbers of Muse cells are isolated from an autologous or allogeneic tissue, these cells may be cultured before cell transplantation until the predetermined number of cells is attained. As previously reported (WO2011/007900), since Muse cells are non-tumorigenic, they are less likely to be cancerous and thus are safe, even if cells collected from a living tissue are contained in undifferentiated states. The collected Muse cells can be cultured in any normal growth medium (e.g., alpha-minimum essential medium (α-MEM) supplemented with 10% calf serum). More specifically, with reference to the above-described WO2011/007900, Muse cells can be cultured and proliferated using an appropriately selected culture medium, additives (e.g., antibiotics, and serum) and the like, to prepare a solution containing Muse cells at a predetermined concentration. When the cell product of the present invention is administered to a human subject, bone marrow aspirates are collected from a human ilium. Then, for example, bone marrow mesenchymal stem cells are cultured as adherent cells obtained from the bone marrow aspirate and proliferated until reaching the cell amount where a therapeutically effective amount of Muse cells can be obtained. Thereafter, Muse cells are isolated using an antigenic marker SSEA-3 as an index to prepare a cell product containing autologous or allogeneic Muse cells. Alternatively, for example, bone marrow mesenchymal stem cells obtained from the bone marrow aspirates can be cultured under external stress conditions, so that Muse cells can be grown and enriched until they reach a therapeutically effective amount, thereby preparing a cell product comprising autologous or allogeneic Muse cells.

When Muse cells are used in a cell product, the cell product may also comprise dimethyl sulfoxide (DMSO), serum albumin and the like for protection of the cells and antibiotics and the like for prevention of contamination and proliferation of bacteria. The cell product may further comprise other pharmaceutically acceptable components (e.g., carriers, excipients, disintegrants, buffer agents, emulsifiers, suspending agents, soothing agents, stabilizers, preservatives, antiseptics, physiological saline). These agents and drugs can be added to the cell product at appropriate concentrations by the skilled person. Thus, Muse cells can also be used as a pharmaceutical composition comprising various additives.

The number of Muse cells contained in the cell product prepared above can be appropriately adjusted to achieve desired effects in treatment of peripheral blood flow disorders, in consideration of, for example, sex, age, and weight of the subject, the condition of the affected area, and the condition of the cells to be used. Individuals as the subject includes, but not limited to, mammals such as human. The cell product of the present invention may be administered multiple times (e.g., 2 to 10 times) at appropriate intervals (e.g., twice a day, once a day, twice a week, once a week, once every two weeks, once a month, once every two months, once every three months, or once every six months) until the desired therapeutic effect is obtained. Thus, the therapeutically effective amount is preferably, for example, 1 to 10 doses of $1\times10^3$ to $1\times10^{10}$ cells/individual/dose, depending on the state of the subject. The total amount administered to an individual is, without limitation, $1\times10^3$ to $1\times10^{11}$ cells, preferably $1\times10^4$ to $1\times10^{10}$ cells, more preferably $1\times10^5$ to $1\times10^9$ cells.

Muse cells to be used in the cell product of the present invention is characterized in that they migrate and engraft to an injured peripheral vascular site. Thus, the site and form of administration of the cell product are not particularly limited. The cell product may be administered locally at or near the site with peripheral blood flow disorder by injection or other methods, or may be administered into a blood vessel by injection or other methods. The type of blood vessel (venous and arterial) into which the cell product is administered is not particularly limited, and is appropriately selected depending on the disease. Preferably, the cell product is injected intravenously. This preference is due to the fact that the therapeutic effect can be sustained for a long time through multiple intravenous injections.

The cell product of the present invention allows for regeneration of blood vessels at the impaired peripheral vascular site in a patient with a peripheral blood flow disorder.

The present invention will be described in more detail with reference to examples below, but is not limited to the examples in any way.

EXAMPLES

Example 1: Preparation of Mouse Model of Lower Limb Ischemia

The experimental protocols using mice in this Example complied with "Regulations on Animal Experiments and Related Activities in Kyoto Prefectural University of Medicine," and the experimental animals were prepared in accordance with the regulations under the supervision of the Animal Experiment Center of Kyoto Prefectural University of Medicine. More specifically, mice were prepared according to the following protocol.

Eight to ten-week female BALB/C nude mice were anesthetized by isoflurane inhalation (4% for induction, and 2% for maintenance). The lower limb was incised, and left common femoral arteries and veins, and left peripheral superficial femoral arteries and veins were ligated with a 5-0 silk suture under a stereoscopic microscope (KONAN OPERATION MICROSCOPE KOM). The mice thus prepared were used as a mouse model of lower limb ischemia in the following experiments.

Example 2: Preparation of Human Muse Cell

Muse cells were obtained according to the method for isolation and identification of human Muse cells described in WO2011/007900. A commercially available mesenchymal stem cell (MSC, Lonza) was used as a source of Muse cells. Muse cells used for transplantation were made to express green fluorescent protein (GFP) to determine whether the cells engraft into the impaired peripheral arterial site. For cell labeling with GFP, Muse cells had been previously transduced with a lentivirus-GFP gene. GFP-labeled Muse cells are isolated as GFP- and SSEA-3-double positive cells by FACS. The remaining cells obtained by isolating Muse cells from MSCs were used as non-Muse cells. GFP-positive MSCs were also isolated by FACS and used as a MSC group.

Example 3: Administration of Cells to Mouse Model of Lower Limb Ischemia

The lower limb ischemia model mice prepared in Example 1 were divided into four groups. At Day 1 after preparation of the model, mice in each group received Muse cells ($3\times10^4$ cells in 100 μL) (Muse), non-Muse cells ($3\times10^4$ cells in 100 μL) (nMuse), MSCs ($2\times10^5$ cells in 100 μL) (BM), or the vehicle (phosphate buffer) (Ve) at two separate locations on the left femoral region. One group included five animals.

Example 4: Laser Doppler Assessment of Lower Limb Blood Flow Over Time

At Days 0, 3, 7, 10, and 14 after preparation of the mouse model of lower limb ischemia, measurement of the blood flow was performed using a two-dimensional laser blood flow imaging apparatus [laser doppler perfusion image (LDPI) analyzer (OMEGAZONE OZ-1, OMEGAWAVE, Inc. Tokyo, Japan). The blood flow in both left and right lower limbs of each individual was measured. The ratio of left side (affected side)/right side (unaffected side) was calculated and considered as LDPI index. As shown in FIG. 1, the improvement of the blood flow in the Muse cell group continued even after Day 14, the blood flow to the ischemic left lower limb was improved to a comparable level with that to the healthy right lower limb. On the other hand, the non-Muse cell (nMuse), MSC (BM), and vehicle (Ve) groups showed certain levels of improvement in the blood flow until Day 10, but not after Day 14.

Figure 2:
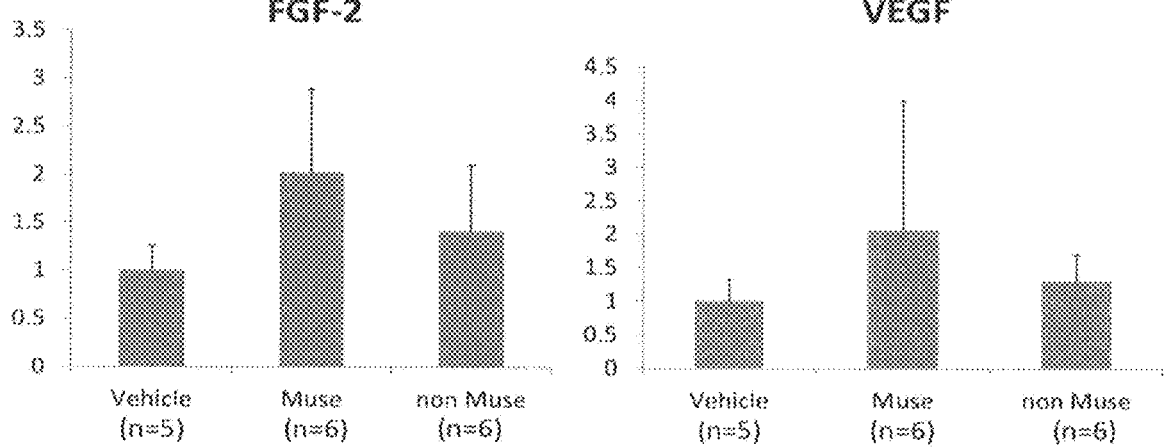
FIG. 2 are graphs showing the results of expression measurement of angiogenesis-related genes as angiogenic factors six days after administration of the cells.

Example 5: Measurement of Expression of Angiogenesis-related Genes as Angiogenic Factors At Day 6 after the cell administration, mRNA was extracted from lower limb skeletal muscles on the left side (affected side). The expression of representative angiogenesis-related genes, VEGF and bFGF (especially, FGF-2) was measured by absolute quantitative real-time RT-PCR. The measurement method was based on Non-patent Document 8. The results are shown in FIG. 2. The Muse cell group showed significantly higher expression of the angiogenesis-related genes as angiogenic factors (mRNA) than that of the vehicle group.

Example 6: Determination of Blood Vessel Density in Ischemic Skeletal Muscle

Figure 3:
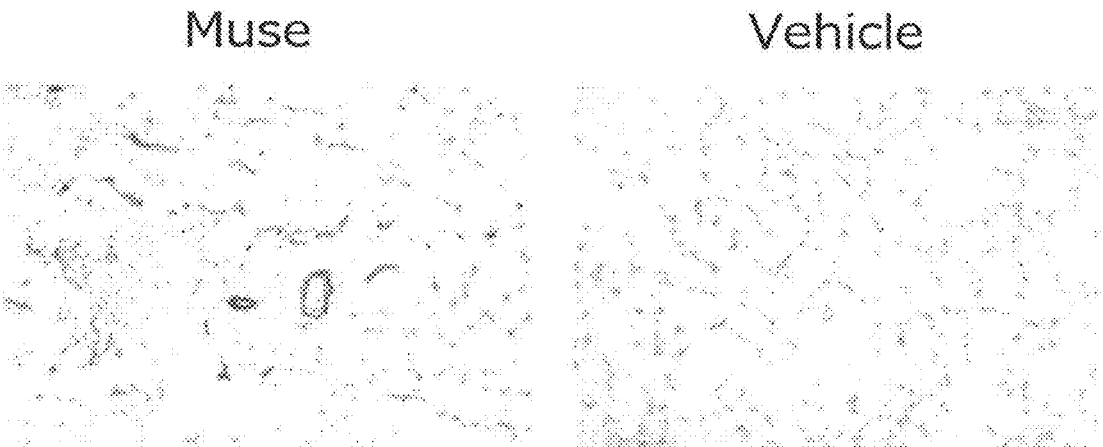
FIG. 3 are pictures showing the results of measurement of blood vessel density in ischemic skeletal muscle 28 days after administration of the cells. The left figure represents administration of Muse cells, and the right figure represents administration of a vehicle.

At Day 28 after the cell administration, the lower limb skeletal muscle tissue on the left side (affected side) was fixed with 4% paraformaldehyde (PFA) to prepare paraffin sections. Then, vascular endothelial cells in the ischemic lower limb skeletal muscle were immunohistochemically stained using an anti-Isolectin GS-IB4 antibody, Alexa Fluor 568 Conjugate (Thermo Fisher Scientific, used in 1:300 dilution) to determine the ratio of vascular endothelial cells per skeletal muscle fiber as the blood vessel density. The results are shown in FIG. 3. It can be seen that the Muse cell group (FIG. 3, left) showed higher blood vessel density in ischemic skeletal muscle than the vehicle group (FIG. 3, right).

Example 7: Evaluation in Wild-Type Mouse Model of Lower Limb Ischemia

Wild-type BALBc mice (12-week males) were used to prepare lower limb ischemia model mice in the same manner as in Example 1. The prepared lower limb ischemia model mice were grouped. At Day 1 after preparation of the model, mice in each group received tail vein (i.v.) or intramuscular (i.m.) injection of Muse cell ($3 \times 10^4$ cells in 200 μL) (Muse), non-Muse cells ($3 \times 10^4$ cells in 200 μL) (non Muse), or bone marrow mononuclear cells ($2 \times 10^5$ cells in 200 μL) (BMMNC). PBS as control was injected into the tail vein. One group included five animals.

Figure 4:
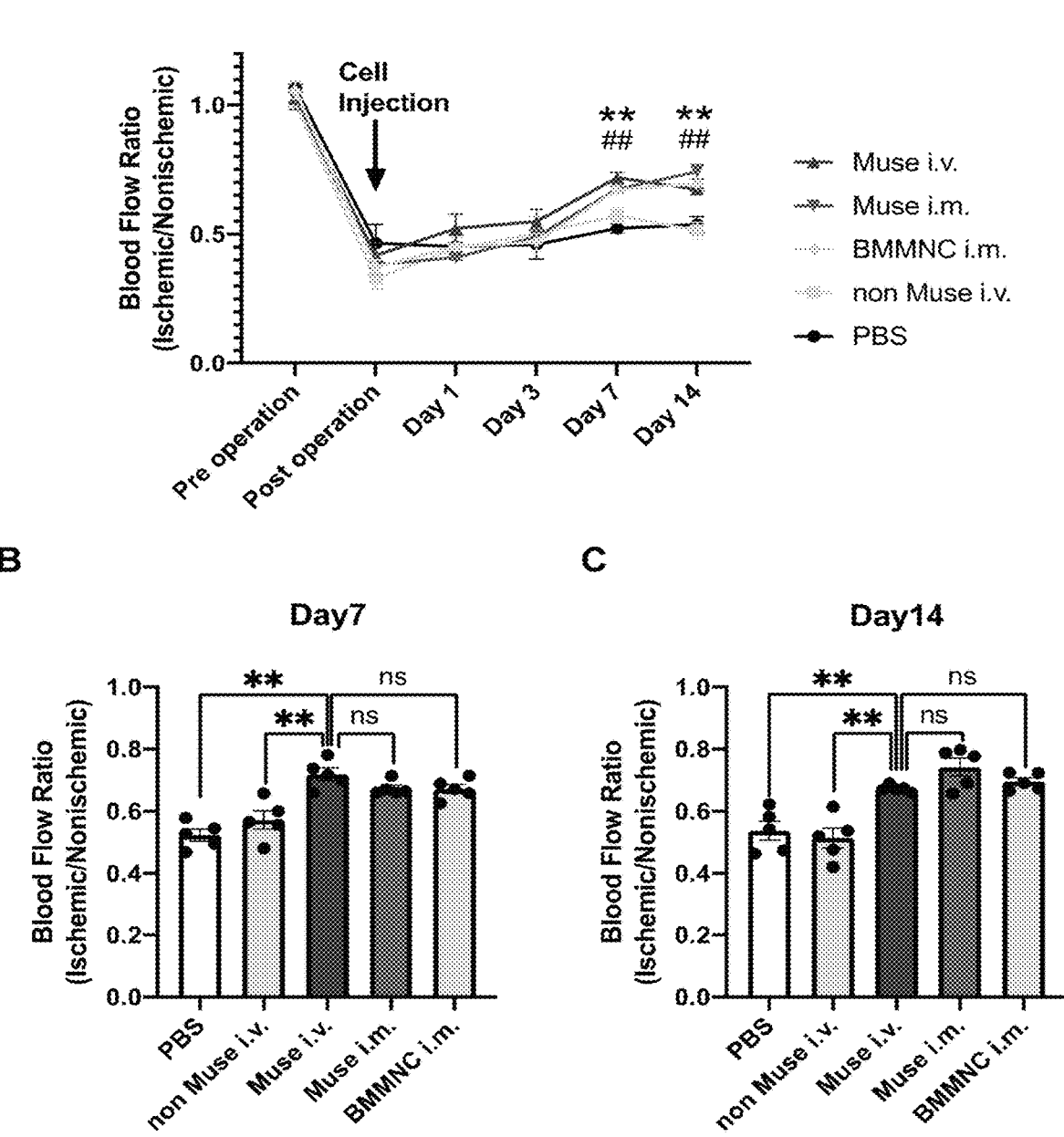
FIG. 4 shows the results of laser doppler velocimetry of blood flow in an ischemic hindlimb of BALBc mice that have received Muse cells, non-Muse cells, BMMNC (bone marrow mononuclear cells), or PBS via intramuscular or intravenous injection. A) Change over time in the ischemic/ non-ischemic limb blood flow ratio ($P<0.01$ for PBS vs. Muse i.v., and ##$P<0.01$ for non Muse i.v. vs. Muse i.v.); B) the blood flow ratio seven days after operation; and C) the blood flow ratio 14 days after operation (significant difference between groups ($P \leq 0.01$)). The results are expressed as mean±SEM (n=5), and the dots in B and C correspond to respective mice.

At pre-operation, immediately post-operation, and Days 1, 3, 7, and 14 post-operation, each group was evaluated for the blood flow using a laser Doppler blood flow meter in the same manner as in Example 4 to determine the blood flows in ischemic hindlimb and non-ischemic hindlimb, and the ratio was calculated. The results are shown in FIG. 4A. The results obtained at Days 7 and 14 were shown in FIGS. 4B and 4C.

The results demonstrate that both intramuscular and intravenous injection of human Muse cells also ameliorated lower limb ischemia in wild-type mice. The intramuscular injection of human Muse cells showed a comparable effect with the intramuscular injection of Muse cells and the intramuscular injection of mouse autologous bone marrow mononuclear cells, suggesting that Muse cells reached and engrafted into the affected area through a vein, resulting in amelioration of ischemia.

Figure 5:
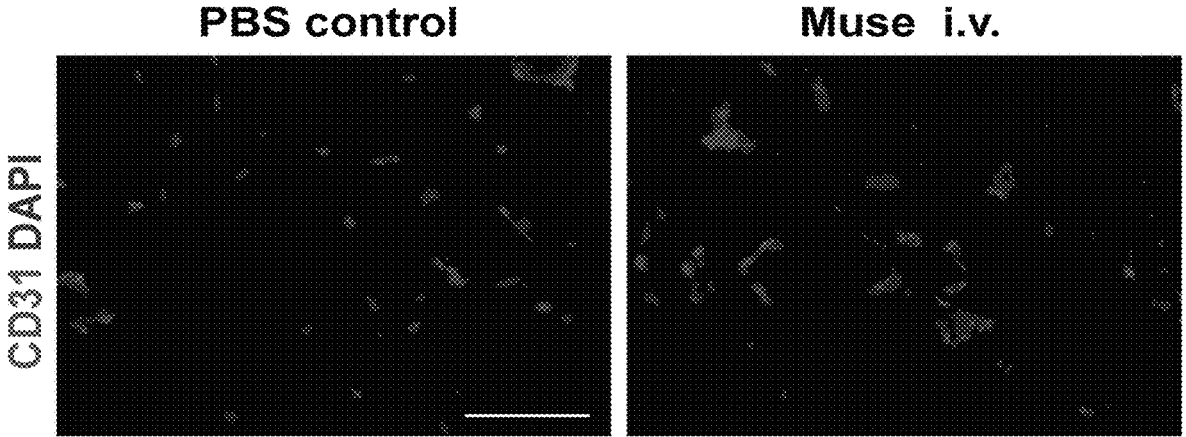
FIG. 5 shows the results (micrographs) of staining of a tissue section of ischemic adductor 14 days after administration of PBS or Muse cells using an anti-CD31 antibody and DAPI. Scale bar: 50 μm.

Next, adductor muscle of mice in the control group or the i.v. Muse cell group was collected at Day 14 post-operation, and was used for tissue analysis. The collected adductor muscle was fixed in 4% PFA for 1 hour, and incubated in 30% sucrose solution overnight. Then, the tissue was embedded in an optimal cutting temperature (OCT) compound (Sakura Finetek), snap-frozen in liquid nitrogen, and sectioned on a cryostat. The tissue section was incubated with a rabbit anti-CD31 (ab182981; Abcam) at 1:5,000 dilution overnight. A goat anti-rabbit Alexa 594 (Abcam) was used as the secondary antibody. The tissue section was mounted with Prolong GOLD Antifade with DAPI (Thermo Fisher Scientific), and then imaged using BZ X800 light microscope (Keyence). The results are shown in FIG. 5. Muse cell-treated group showed significantly increased expression of CD31, a marker for endothelial cell, suggesting that Muse cells promoted angiogenesis in ischemic hindlimb and improved the ischemic state.

INDUSTRIAL AVAILABILITY

The cell product of the present invention can be administered to a subject suffering from a peripheral blood flow disorder such as a peripheral arterial disease, resulting in accumulation and engraftment to the impaired peripheral vascular site, and reconstruction of blood vessels in the impaired peripheral vascular site, thereby ameliorating or treating blood flow disorders in the peripheral vascular site.

The invention claimed is:

1. A method for treating a peripheral blood flow disorder, the method comprising:

intravenously administering, to a patient in need thereof, a therapeutically effective amount of an SSEA-3-positive pluripotent stem cell which is a Muse cell isolated or enriched from a mesenchymal tissue in a living body or a cultured mesenchymal cell comprising mesenchymal stem cells, wherein the SSEA-3-positive pluripotent stem cell is isolated from the mesenchymal tissue in the living body or the cultured mesenchymal cell by using an antigenic marker SSEA-3 as an index or enriched from the mesenchymal tissue in the living body or the cultured mesenchymal cell by culturing under external stress condition, and wherein the SSEA-3-positive pluripotent stem cell is one having all of the following characteristics:

(i) having low telomerase activity;

(ii) capable of differentiating into any of tridermic cells;

(iii) showing no neoplastic proliferation; and (iv) having self-renewal capacities, and wherein the method increases expression of CD31 and improves ischemic state in the patient, as compared to when non-Muse cells which are remaining stem cells obtained by isolating the SSEA-3-positive pluripotent stem cell from the mesenchymal stem cells are administered.

2. The method of claim 1, wherein the peripheral blood flow disorder is a peripheral arterial disease.

3. The method of claim 2, wherein the peripheral arterial disease is chronic arterial obstruction in a limb.

4. The method of claim 2, wherein the peripheral arterial disease is arteriosclerosis obliterans.

5. The method of claim 2, wherein the peripheral arterial disease is thromboangiitis obliterans (Buerger's disease).

6. The method of claim 2, wherein the peripheral arterial disease is popliteal artery entrapment syndrome.

7. The method of claim 1, wherein the SSEA-3-positive pluripotent stem cell is one having all of the following characteristics:

(i) SSEA-3-positive;

(ii) CD105-positive;

(iii) having low telomerase activity;

(iv) capable of differentiating into any of tridermic cells;

(v) showing no neoplastic proliferation; and (vi) having self-renewal capacities.

8. The method of claim 1, wherein the SSEA-3-positive pluripotent stem cell is one having all of the following characteristics:

(i) having no telomerase activity;

(ii) capable of differentiating into any of tridermic cells;

(iii) showing no neoplastic proliferation; and (iv) having self-renewal capacities.

9. The method of claim 1, wherein the SSEA-3-positive pluripotent stem cell is one having all of the following characteristics:

(i) SSEA-3-positive;

(ii) CD105-positive;

(iii) having no telomerase activity;

(iv) capable of differentiating into any of tridermic cells;

(v) showing no neoplastic proliferation; and (vi) having self-renewal capacities.

10. The method of claim 1, wherein the therapeutically effective amount of the SSEA-3-positive pluripotent stem cell is $1 \times 10^3$ to $1 \times 10^{10}$ cells/individual/dose.

11. The method of claim 1, wherein ischemia is ameliorated by both intramuscular and intravenous injection.

12. The method of claim 1, wherein improvement of blood flow continues after 14th day from the administration.

13. The method of claim 1, wherein mRNA expression of angiogenesis-related genes is higher than that of a vehicle administered group.

14. The method of claim 1, wherein blood vessel density of ischemic skeletal muscle is higher than that of a vehicle administered group.

* * * * *